United States Patent
Chen et al.

(10) Patent No.: US 12,090,132 B2
(45) Date of Patent: Sep. 17, 2024

(54) TRIS DBA PHARMACEUTICAL COMPOSITION AND ITS USE FOR TREATING AUTOIMMUNE DISEASES

(71) Applicant: National Defense Medical Center, Taipei (TW)

(72) Inventors: Ann Chen, Taipei (TW); Shuk-Man Ka, Taipei (TW)

(73) Assignee: NATIONAL DEFENSE MEDICAL CENTER, Taipei (TW)

(*) Notice: Subject to any disclaimer, the term of this patent is extended or adjusted under 35 U.S.C. 154(b) by 69 days.

(21) Appl. No.: 16/928,613

(22) Filed: Jul. 14, 2020

(65) Prior Publication Data
US 2021/0186919 A1 Jun. 24, 2021

(30) Foreign Application Priority Data
Dec. 24, 2019 (TW) ................ 108147439

(51) Int. Cl.
*A61K 31/28* (2006.01)
*A61P 29/00* (2006.01)
*A61K 9/00* (2006.01)

(52) U.S. Cl.
CPC .............. *A61K 31/28* (2013.01); *A61P 29/00* (2018.01); *A61K 9/0053* (2013.01)

(58) Field of Classification Search
CPC ................. A61K 31/28; A61P 29/00
See application file for complete search history.

(56) References Cited

U.S. PATENT DOCUMENTS

2014/0127231 A1* 5/2014 Teuscher ............ A61K 31/7105
514/17.9

FOREIGN PATENT DOCUMENTS

WO WO-2008076965 A1 * 6/2008 ............. A61K 31/28

OTHER PUBLICATIONS

Wu et al (J Immunol, 2020; 204:1448-1461, published on line Feb. 2020) (Year: 2020).*
Roep et al (Nat Med, 2012; 18:48-53) (Year: 2012).*
Chan et al (Nat. Rev. Nephrol, 2015; 11:46-61) (Year: 2015).*
Brent et al (Lupus Nephritis, Medscape; Updated Dec. 7, 2017, https://emedicine.medscape.com/article/330369-overview, Internet Archive Wayback Machine date, Jun. 24, 2018) (Year: 2017).*

* cited by examiner

*Primary Examiner* — Rayna Rodriguez
(74) *Attorney, Agent, or Firm* — Muncy, Geissler, Olds & Lowe, P.C.

(57) ABSTRACT

The invention relates to a new use of Tris (dibenzylideneacetone) dipalladium (Tris DBA). The invention provides a pharmaceutical composition comprising Tris DBA, and a use of the pharmaceutical composition for treating autoimmune diseases, such as, Multiple sclerosis, psoriasis, asthma, systemic lupus erythematosus and lupus nephritis.

4 Claims, 27 Drawing Sheets

Figure

TRIS DBA PHARMACEUTICAL COMPOSITION AND ITS USE FOR TREATING AUTOIMMUNE DISEASES

CROSS-REFERENCE TO RELATED APPLICATIONS

This Non-provisional application claims priority under 35 U.S.C. § 119(a) on Patent Application No(s). 108147439 filed in Taiwan, Republic of China on Dec. 24, 2019, the entire contents of which are hereby incorporated by reference.

FIELD OF INVENTION

The invention relates to a new medical use of Tris DBA, and more particularly to use of pharmaceutical composition of Tris DBA for treating autoimmune diseases, especially lupus nephritis.

BACKGROUND OF INVENTION

The Systemic Lupus Erythematosus (SLE) is an autoimmune disease which endangers lives, it is characterized by forming autoantibodies in vivo against different tissues, generally against DNA. The SLE affects about 140,000 persons in the U.S. and 105,000 persons in Western Europe, most of them are women of childbearing age.

The feature of SLE is inflammation, mainly affecting connective tissue, including skin, joints and organ system. The generally affected organs include kidneys, heart, lungs and central nervous system. The clinical manifestations of SLE include general disease, pain, rash, cognitive impairment, thrombosis, anemia, pleurisy, gastrointestinal dysfunction and abortion. In most patients, the lupus correlated immunoglobulin and immune complex deposit in glomeruli, degrading renal function. The lupus patients account for 70% of moderate to serious SLE patients, half of patients have nephritis, their urine contains protein. Some patients can be treated by using immunosuppressants and/or cytotoxic drugs, but the clinical response to these drugs may be transient, and the medication will induce adverse side effects, and many patients are irresponsive to pharmacotherapy. A part of patients will develop into renal failure, and then they must receive hemodialysis all their life long, or seek for renal transplantation.

SUMMARY OF THE INVENTION

In view of this, in order to solve the above problems, the circle desires a safe and effective drug to treat autoimmune diseases, especially lupus nephritis. Therefore, the present invention provides a new medical use of Tris DBA pharmaceutical composition for preparing drugs for treating and preventing autoimmune diseases.

The present invention provides a use of Tris DBA pharmaceutical composition for preparing drugs for treating or preventing autoimmune diseases.

In an embodiment of the present invention, the autoimmune diseases include arthritis, rheumatoid arthritis, psoriasis, Chronic Obstructive Pulmonary Disease (COPD), Systemic Lupus Erythematosus (SLE), lupus nephritis, asthma, multiple sclerosis and/or cystic fibrosis.

In an embodiment of the present invention, the autoimmune disease is lupus nephritis.

In an embodiment of the present invention, the Tris DBA pharmaceutical composition inhibits cellular autophagy or inflammatory reaction.

In an embodiment of the present invention, the Tris DBA pharmaceutical composition has antioxidation.

In an embodiment of the present invention, the Tris DBA pharmaceutical composition is in the form of granule, capsule, pastille, powder, solution or suspension.

In an embodiment of the present invention, the Tris DBA pharmaceutical composition is applied by oral administration, percutaneous administration, pernasal administration, hypodermic injection, intravenous injection, intramuscular injection or intraperitoneal injection.

In an embodiment of the present invention, an effective dose of the Tris DBA pharmaceutical composition is applied to a subject, wherein the subject is a mammal.

In an embodiment of the present invention, the mammal is a mouse, the effective dose is 10-20 mg/kg.

In an embodiment of the present invention, the mammal is a human, the effective dose is 600-1200 mg/kg.

In an embodiment of the present invention, the Tris DBA pharmaceutical composition for immune diseases is used for inhibiting phosphorylation of mitogen-activated protein kinase (MAPK).

In an embodiment of the present invention, the Tris DBA pharmaceutical composition comprises one or more extra active ingredients, the extra active ingredients comprises an immunosuppressant, an immunomodulator, an anti-inflammatory, a MAPK inhibitor, an antioxidant and/or an autophagy accelerant.

BRIEF DESCRIPTION OF THE DRAWINGS

FIG. 1D shows the resulting image of Western Blot.

DETAILED DESCRIPTION OF THE INVENTION

Figure 1A:
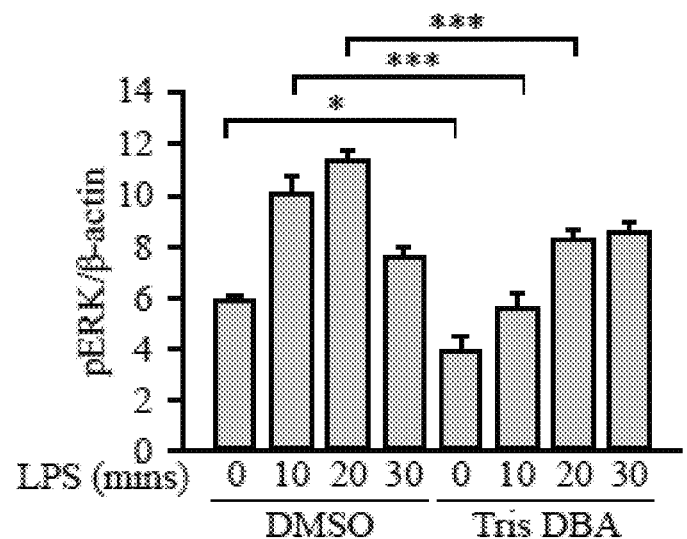
FIGS. 1A-1D shows that the Tris DBA can inhibit the phosphorylation of pERK (FIG. 1A), pJNK (FIG. 1B) and pp38 (FIG. 1C) proteins on the MAPK information transfer path in J774A.1 cells.
Figure 1B:
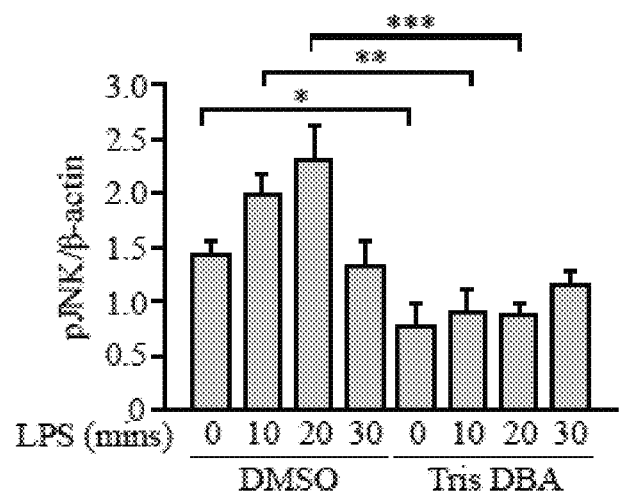
Figure 1C:
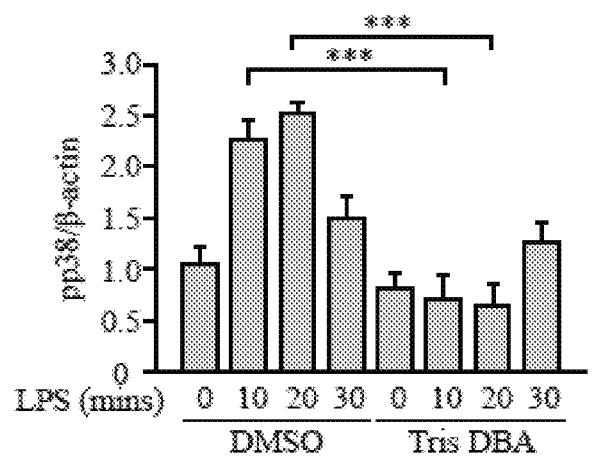
Figure 1D:
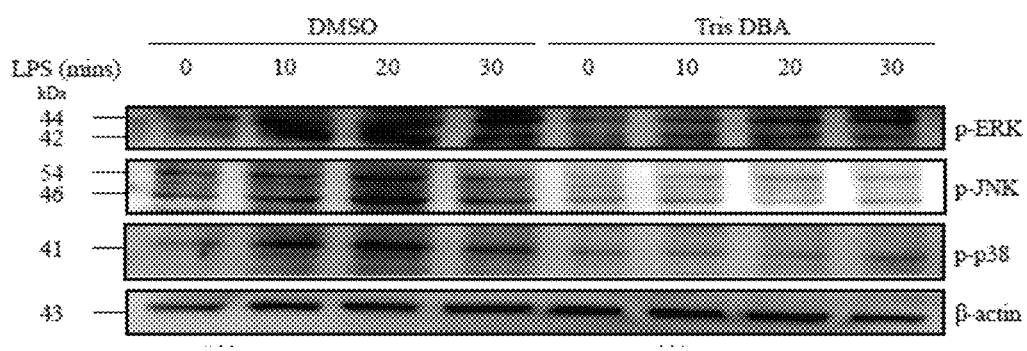

The present invention provides a Tris DBA pharmaceutical composition and its new medical application. The Tris DBA pharmaceutical composition of the present invention comprises an effective dose of Tris DBA and a pharmaceutically acceptable carrier.

Said "effective dose" or "therapeutically effective dose" of the present invention refers to the quantity applied to an individual which can effectively, at least partially improve the condition of an individual. Said "individual" of the present invention refers to animal, preferably to mammal, and the mammal can be human or nonhuman animal.

The source of Tris DBA in the present invention is not limited, it can be chemically synthesized or commercially available, as long as it has the same chemical structure and activity.

Said carriers in the present invention include but not limited to excipient, diluent, assistant, stabilizer, absorption retarder, disintegrant, solubilizer, emulsifier, antioxidant, adhesive, binder, tackifier, dispersant, suspending agent, lubricant and hygroscopic agent. The dosage form applicable to oral administration is taken as an example, the carrier examples include but not limited to water, saline solution, dextrose, glycerol, ethanol or analogs, cellulose, starch, sugar bentonite, and the combinations thereof. Any suitable method can be used, the medicament is provided in the dosage form fit for oral administration, such as pastille, pill, capsule, granule and powder in solid form, or oral liquid, syrup, spirit, elixir and tincture in liquid form.

The pharmaceutical composition of the present invention can be in any suitable form, no special limitation, the suitable dosage form is selected according to the desired use. For example, but not limited to this, the medicament can be applied to the individual in need by oral administration or non-oral administration (e.g. percutaneous administration, pernasal administration, hypodermic injection, intravenous injection, intramuscular injection, intraperitoneal injection, subcutaneous implantation or interstitial implantation) for prevention and treatment. According to the form and use, as long as the selected carrier has no adverse effect on Tris DBA. The carrier can be excipient, diluent, assistant, stabilizer, absorption retarder, disintegrant, solubilizer, emulsifier, antioxidant, adhesive, binder, tackifier, dispersant, suspending agent, lubricant and hygroscopic agent.

The pharmaceutical composition of the present invention can treat, prevent or improve autoimmune diseases and inflammatory symptoms, especially autoimmune inflammatory symptoms, such as arthritis (e.g. rheumatoid arthritis, chronic progressive arthritis and deforming arthritis) and rheumatic disease, including inflammatory symptoms and rheumatic disease concerning bone loss, inflammatory pain, vertebral arthropathy (including ankylosing spondylitis), Reiter syndrome, reactive arthritis, psoriatic arthritis, juvenile idiopathic arthritis and enteropathic arthritis, enthesitis, allergy (including tracheal allergy and epidermic allergy) and anaphylaxis. The antibody of the present invention can be applied to specific autoimmune diseases, including autoimmune blood diseases (e.g. hemolytic anemia, aplastic anemia, pure red cell anemia and idiopathic thrombocytopenia), SLE, lupus nephritis, inflammatory muscular disease (dermatomyositis), periodontitis, polychondritis, scleroderma, Wegener granulomatosis, dermatomyositis, chronic active hepatitis, myasthenia gravis, psoriasis, Steven-Johnson syndrome, idiopathic sprue, autoimmune inflammatory enteropathy (e.g. ulcerative colitis, Crohn's disease and irritable bowel syndrome), endocrinic eye disease, Graves' disease, sarcoidosis, multiple sclerosis, systemic sclerosis, fibrotic disease, primary biliary cirrhosis, juvenile diabetes mellitus (Type I diabetes mellitus), uveitis, keratoconjunctivitis sicca and vernal keratoconjunctivitis, pulmonary interstitial fibrosis, phantom osteolysis, multiple myeloma, other types of inflammatory diseases of tumor, skin and cornea, skeleton implant looseness, dysbolism (e.g. obesity, atherosclerosis and other cardiovascular diseases, including dilated cardiomyopathy, myocarditis, Type II diabetes mellitus and blood lipid abnormality), and autoimmune thyroid diseases (e.g. Hashimoto thyroiditis, primary vasculitis of small and moderate blood vessels, trunk vasculitis (including giant cell arteritis), suppurative hidradenitis, ophthalmoneuromyelitis, Sjogren's syndrome, Behcet's disease, atopic and contact dermatitides, bronchiolitis, inflammatory muscular disease, autoimmune peripheral neuropathy, immune kidney, liver and thyroid diseases, inflammation and atherosclerosis, autoinflammatory fever syndrome, immune blood disease and bullous diseases of skin and mucous membrane.

In an embodiment, the pharmaceutical composition of the present invention can treat, prevent or improve multiple sclerosis, psoriasis, asthma, SLE and lupus nephritis, optimally lupus nephritis.

In an embodiment, the pharmaceutical composition of the present invention can inhibit the autophagy of cells and inflammatory reaction. In another embodiment, the pharmaceutical composition of the present invention can promote the antioxidation of cells.

In the pharmaceutical composition of the present invention, Tris DBA can be the unique active constituent or combined with other drugs (e.g. immunosuppressant, immunomodulator or anti-inflammatory). In an embodiment, Tris DBA can be combined with DMARD (e.g. auric salt, sulphasalazine, antimalarias, methotrexate, D-penicillamine, azathioprine, mycophenolic acid, tacrolimus, sirolimus, minocycline, leflunomide, glucocorticoid); calcineurin inhibitor (e.g. cyclosporin A or FK 506); lymphocyte recirculation regulator (e.g. FTY720 and FTY720 analogs); mTOR inhibitor (e.g. rapamycin, 40-O-(2-ethoxyl)-rapamycin, CCI779, ABT578, AP23573 or TAFA-93); ascomycin with immunosuppression property (e.g. ABT-281, ASM981); corticosteroid; endoxan; azathioprine; leflunomide; mizoribine; myco-pheno-late mofetil; 15-deoxyspergualine or immunosuppressive homolog, analog or derivant thereof, immunosuppressive monoclonal antibody (e.g. monoclonal antibody against white blood cell receptor, e.g. MHC, CD2, CD3, CD4, CD7, CD8, CD25, CD28, CD40, CD45, CD58, CD80, CD86 or ligand thereof); adhesive molecule inhibitor (e.g. LFA-1 antagon, ICAM-1 or ICAM-3 antagon, VCAM-4 antagon or VLA-4 antagon); or anti-TNF agent (e.g. monoclonal antibody against TNF, e.g. infliximab, adalimumab, CDP870); or receptor constructor against TNF-RI or TNF-RII (e.g. Etanercept, PEG-TNF-RI)); pro-inflammatory cytokines blocking agent, IL1 blocking agent, IL13 blocking agent, L4 blocking agent, IL6 blocking agent, other IL17 blocking agent; chemotactic factor blocking agent (e.g. inhibitor or activator for protease (metalloprotease), anti-L15 antibody, anti-L6 antibody, anti-TL4 antibody, anti-IL13 antibody, anti-CD20 antibody); NSAID (e.g. aspirin).

The therapeutically effective dose will be determined according to the severity and course of disease, prior therapy, patient's health status, body weight and response to drug and the doctor's judgment. The preventively effective dose is determined according to the patient's health status, body weight, severity and course of disease, prior therapy, response to drug and doctor's judgment.

In an embodiment, the pharmaceutical composition of the present invention can be applied to the patient three times a day, two times a day, once a day, every other day or every three days. In some embodiments, the administration can be performed discontinuously and regularly. In other embodiments, the pharmaceutical composition of the present invention is applied to the patient only if a specific symptom occurs, e.g. pain, fever, inflammation or skin disease. The administration schedule of different compounds can be determined according to other compounds or unrelated to other compounds.

Generally speaking, the general dose for adults is 600 mg/kg to 1200 mg/kg. The required dose can be applied in the form of single dose or in the form of fractionated dose simultaneously (or in a short time), or at proper intervals, e.g. twice, three times, four times or more than four times per day. In some embodiments, the therapeutic dose of Tris DBA is 600 mg/to 800 mg/day, preferably 800 mg/day to 1000 mg/day, optimally 1000 mg/day to 1200 mg/day.

Example 1: Test for Effect of Tris DBA on Inhibiting NLRP3 Inflammasome Activation In order to prove the effect of Tris DBA on inhibiting NLRP3 inflammasome activation, the present invention used mouse macrophage strain J774A.1 to analyze the effect of Tris DBA on NLRP3 inflammasome, and used rapamycin as control group. Each group was treated with 0, 0.1, 0.5 and 1 μM Tris DBA culture medium for 30 minutes, reacting with 1 μg/ml lipopolysaccharide (LPS) of NLRP3 inflammasome typical activator for 5.5 hours. Finally, it reacted with 5 mM ATP reagent for 30 minutes, the IL-1β and caspase-1 cytokines were tested by ELISA.

The protein expression was analyzed by Western Blot, the cells and Tris DBA were cultured for 1 hour, and cultured with two groups with LPS or without LPS respectively for 5.5 hours to test the expression level of cytokines (NLRP3, caspase-1, pro-caspase-1, pro-IL-1β, pro-IL-1β) in cells. This step refers to the data from prior literature (Chang Y P, et. al. 2015. Resveratrol inhibits NLRP3 inflammasome activation by preserving mitochondrial integrity and augmenting autophagy.

The cell strain J774A.1 is treated with Tris DBA and antioxidant (NAC) respectively for one hour, the ROS generation is tested by commercial reagent H2DCFDA.

Figure 1E:
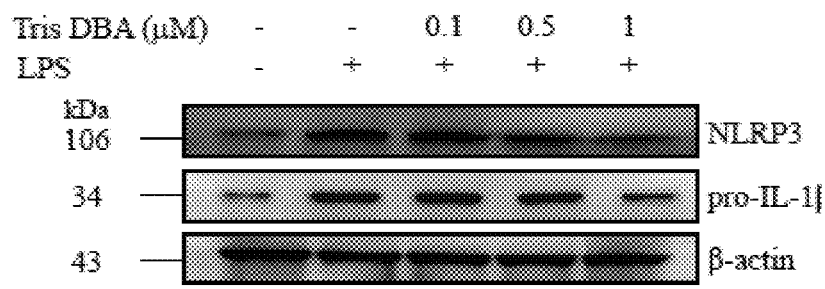
FIG. 1E shows the resulting image of Western Blot, showing the quantity of NLRP3 (FIG. 1F) and pro-IL-1β (FIG. 1G) in J774A.1 cells that can be inhibited by Tris DBA.
Figure 1F:
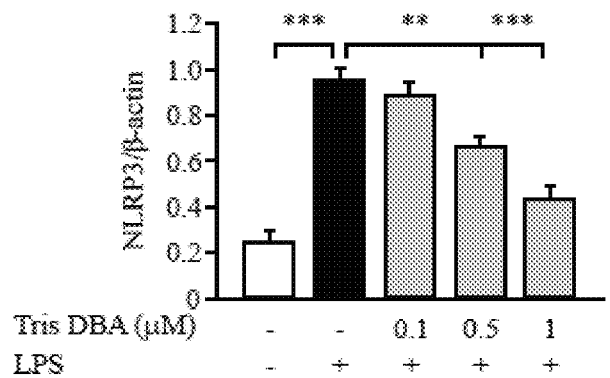
FIG. 1H shows that the Tris DBA can inhibit the formation of ROS in J774A.1 cells.
FIG. 1I shows that the Tris DBA will not affect the activity of NF-κB in J774A.1 cells.
Figure 1G:
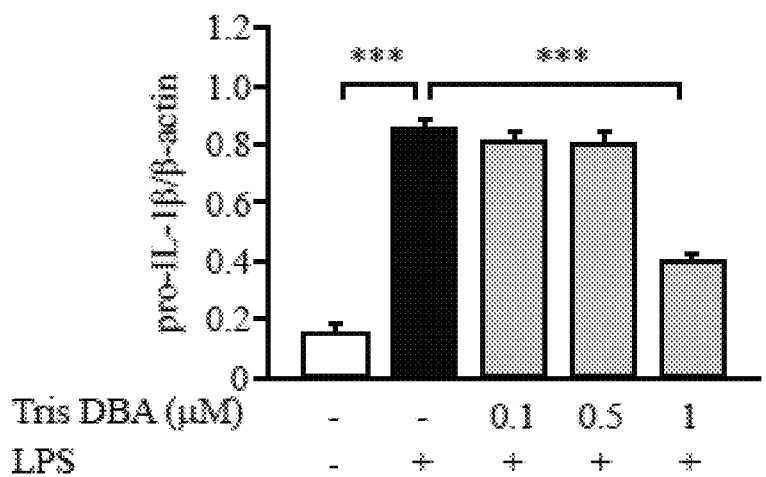
Figure 1H:
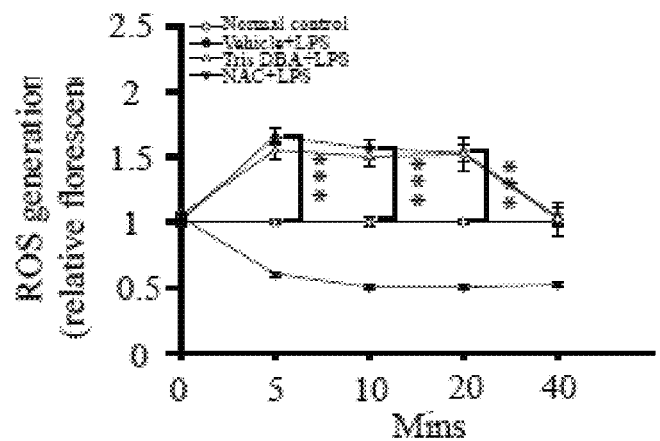
Figure 1I:
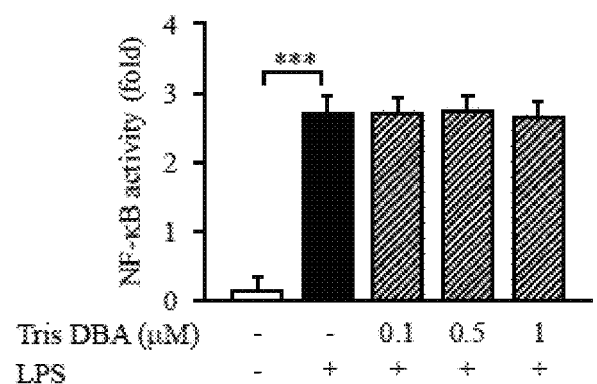

As shown in FIGS. 1A-1D, the results show that Tris DBA can inhibit the pERK, pJNK and pp38 expression levels, as well as NLRP3 and pro-IL-1β protein expression levels (FIG. 1E-1G). As shown in FIGS. 1H-1I, Tris DBA fails to inhibit the ROS and NF-κB activation.

Figure 2A:
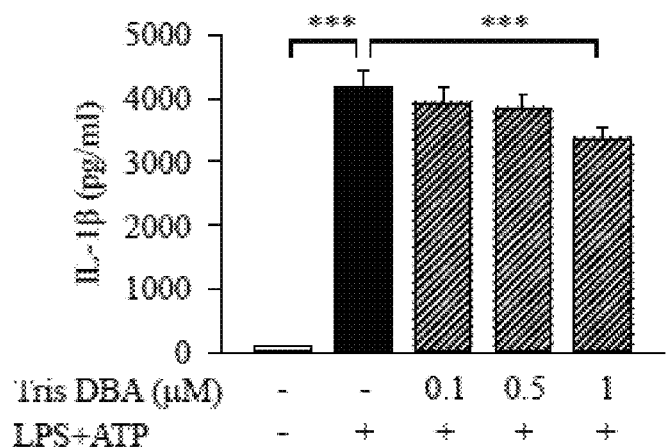
FIG. 2A shows that Tris DBA can inhibit IL-1β induced by LPS in J774A.1 cells.
Figure 2B:
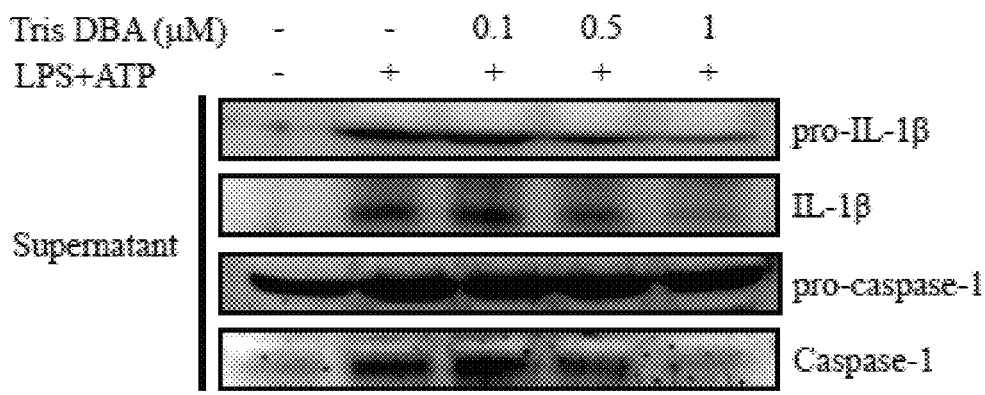
FIG. 2B shows that Tris DBA can inhibit the cytokines induced by LPS in J774A.1 cells.
Figure 2C:
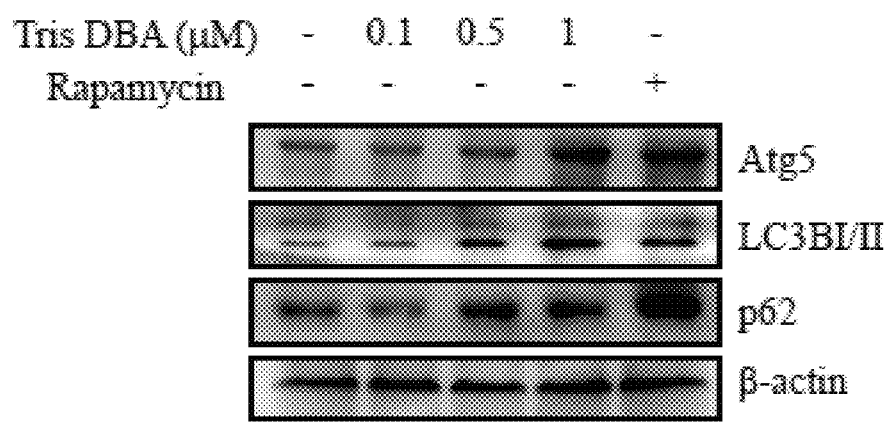
FIGS. 2C-2F Western Blot resulting images show that Tris DBA can promote the manifestation of autophagy factorsAtg5 (FIG. 2D), LC3BI/II (FIG. 2E) and p62 (FIG. 2F) in J774A.1 cells.
Figure 2D:
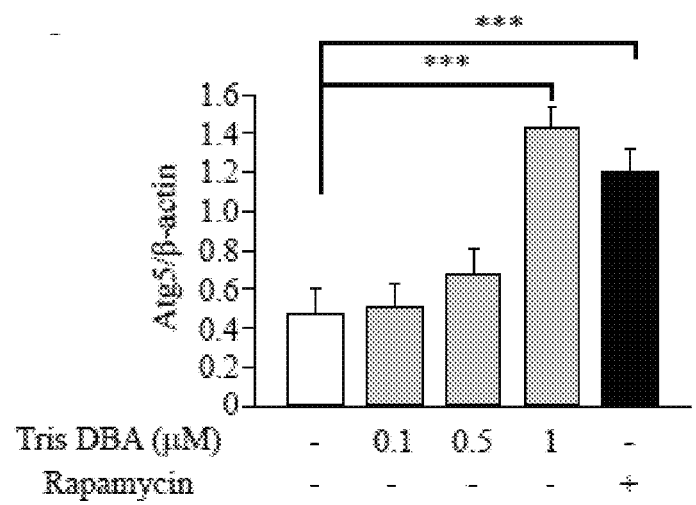
Figure 2E:
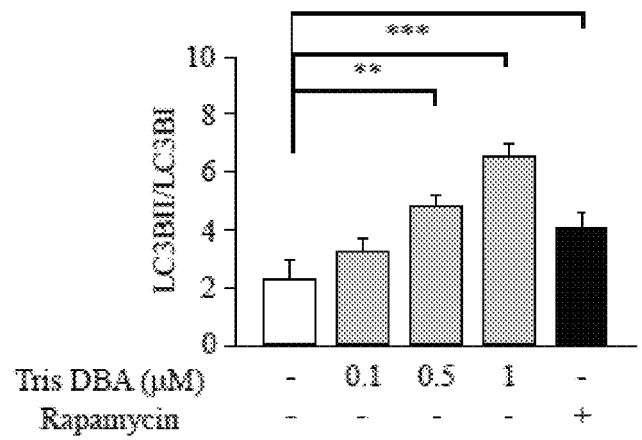
Figure 2F:
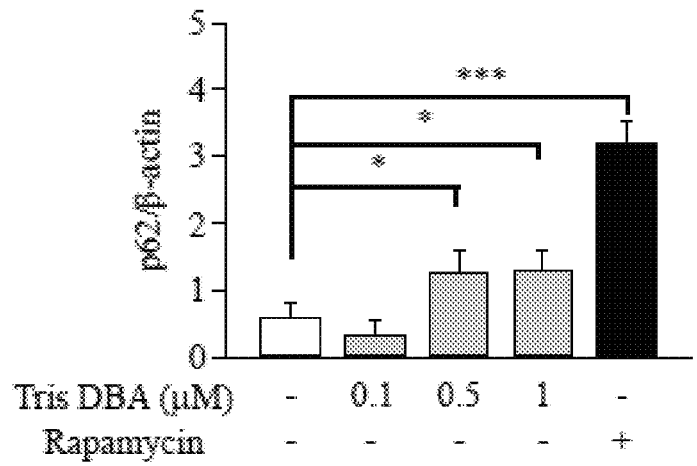
Figure 2G:
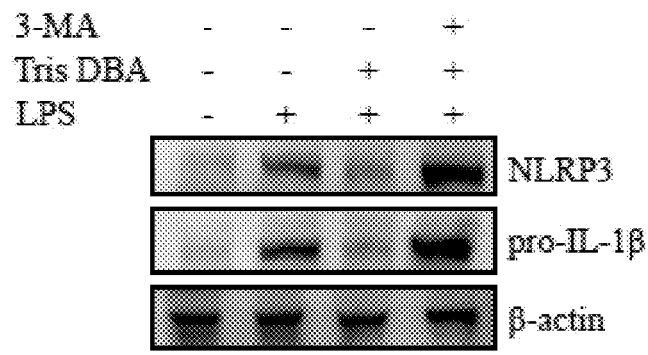
FIGS. 2G-2I, the results show that Tris DBA can inhibit NLRP3 inflammation expression level.
Figure 2H:
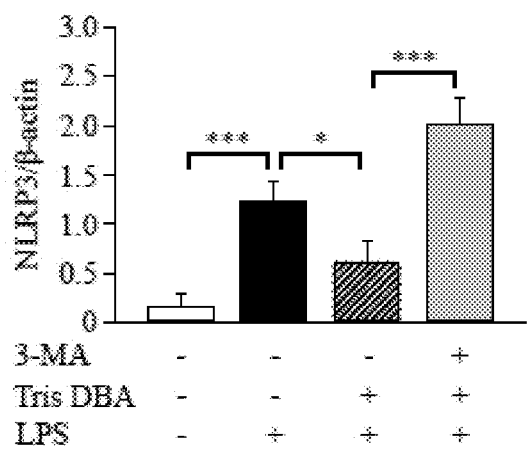
Figure 2I:
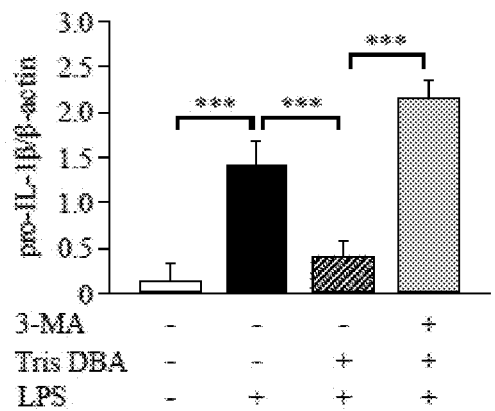
Figure 2J:
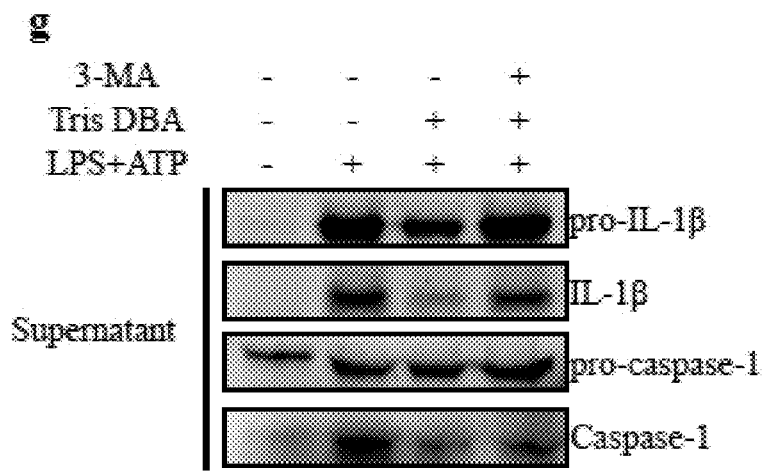
FIGS. 2J-2K, the results show that Tris DBA can inhibit the expression level of IL-1β in J774A.1 cells.
Figure 2K:
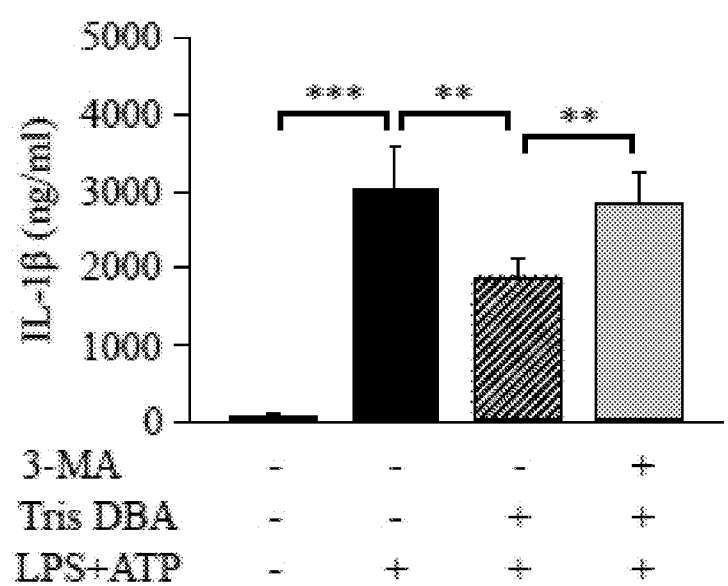

As shown in FIG. 2A, the result shows after the treatment with ATP (NLRP3 inflammasome initiating agent), the Tris DBA compound can promote autophagy and further inhibit the activation of NLRP3 inflammasome. As shown in FIG. 2B, the IL-1β, caspase-1, pro-IL-1β and pro-IL-1β of cell supernatant are tested by Western Blot. The result shows that Tris DBA can inhibit the cytokines induced by LPS in J774A.1 cells. As shown in FIGS. 2C-2F, FIG. 2C shows that Tris DBA promotesAtg5, LC3BI/II and p62 expression levels and it is concentration-dependent, compared with control group Rapamycin group, Tris DBA can promote the manifestation of autophagy factors Atg5 (FIG. 2D), LC3BI/II (FIG. 2E) and p62 (FIG. 2F) in J774A.1 cells. As shown in FIGS. 2G-2I, the cellular autophagy inhibitor 3-Ma and Tris DBA can inhibit the NLRP3 inflammation expression. FIGS. 2J-2K show that Tris DBA can inhibit the expression level of IL-1β in J774A.1 cells.

To sum up, Tris DBA can reduce the activation signal of MAPK (ERK, INK) induced NLRP3 inflammasome and enhance autophagy to inhibit NLRP3 inflammation.

Example 2. Improve Mouse Animal Model of Accelerated Aggravated Lupus Nephritis

Improve mouse animal model of accelerated aggravated lupus nephritis8-week-old female mouse (NZB/WF1) model is used for experiment in this embodiment, the mice are randomly divided into two groups (treatment group Tris DBA, negative control group Katimin-1), 7 mice per group, the LPS (0.6 mg/kg) is injected into the abdominal cavity of mouse twice a week, the Tris DBA (30 mg/kg) or Katimin-1® is applied by intraperitoneal injection in one week after injection, the mice are sacrificed in Week 3 and Week 5 respectively.

2.1 Effect of Tris DBA on Inhibiting Activation of BMDCs and Proliferation of T Cells First of all, the mouse BMDCs are abstracted from the 8-week-old mouse to analyze the effect of Tris DBA on inflammatory factor. The BMDC cells are mixed with 1 μg/mL LPS to stimulate the formation of inflammatory factor, after 0, 0.1, 0.5 and 1 μM Tris DBA are processed, different labelled antibodies of CD11c/CD80 or CD11c/CD86 are processed, the expression level of dendritic cell surface antigen is tested by flow cytometer.

The CD4 T cells of OVA-TCR transgenic mouse and T cell proliferation of antigenic specificity are used to analyze the manifestation of dendritic cell antigen. The OVA323-339 peptide reacts with LPS and LPS+Tris DBA groups for 16 hours respectively. The CD4 T cells abstracted from OVA-TCR transgenic mouse are cultured with BMDCs as per ratios of 1:0, 1:1, 1:2 and 1:4, the T cell proliferation is determined by radioactive [3H]-thymidine, and the processed cell supernatant is used for testing the IFN-γ and IL-4 expression levels in Th1 and Th2 cells according to the operational manual of commercial reagent kit.

Figure 3A:
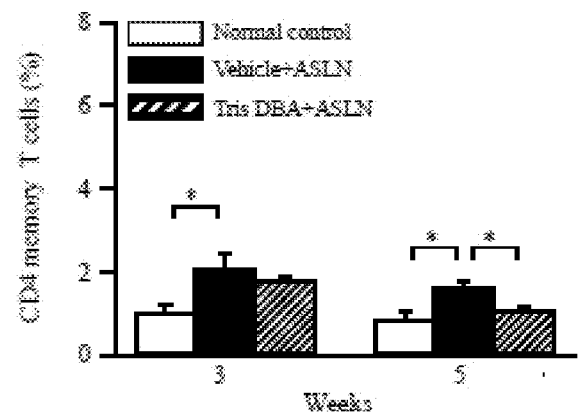
FIGS. 3A-3B show that Tris DBA inhibits the CD4+ memory T cells and CD8+ memory T cells in ASLN mouse spleen.
Figure 3B:
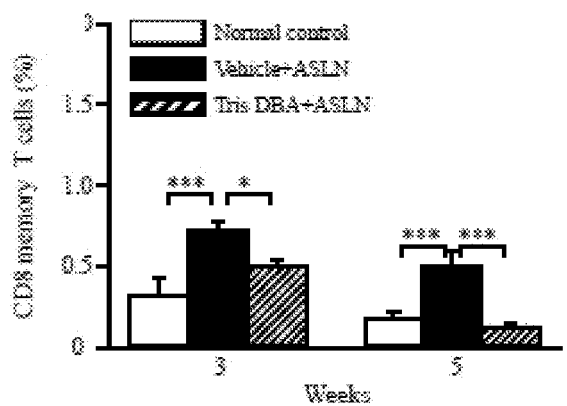
Figure 3C:
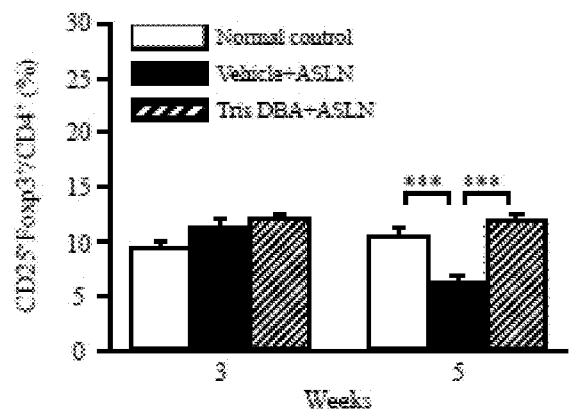
FIGS. 3C-3D show that Tris DBA will not inhibit the proliferation of CD4+CD25+Foxp3+Treg cells and T cells in ASLN mouse kidney.
Figure 3D:
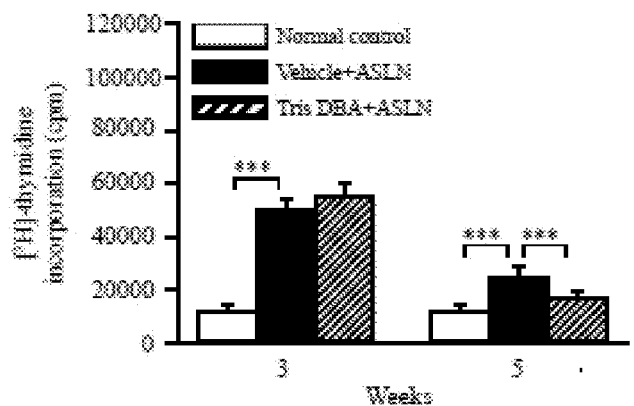
Figure 3E:
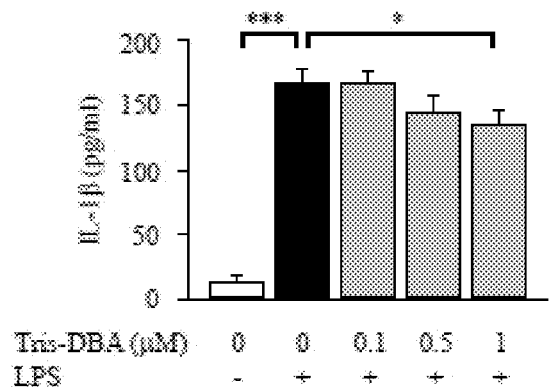
FIGS. 3E-3L show that Tris DBA inhibits IL-1 (FIG. 3E), TNF-α (FIG. 3F), IL-6 (FIG. 3G), CD80+ (FIG. 3H), CD86+ (FIG. 3I), IFN-γ (FIG. 3J) and IL-4 (FIG. 3K) in T cells, and inhibits the proliferation of T cells (FIG. 3L).
Figure 3F:
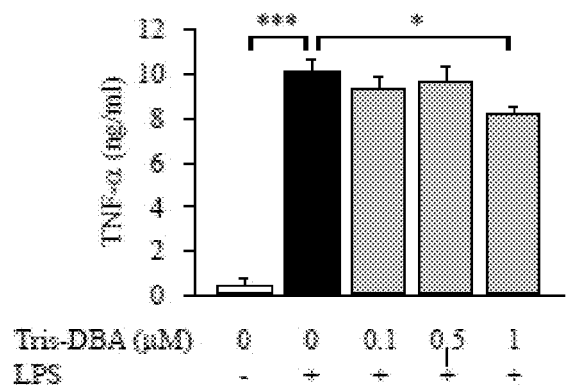
Figure 3G:
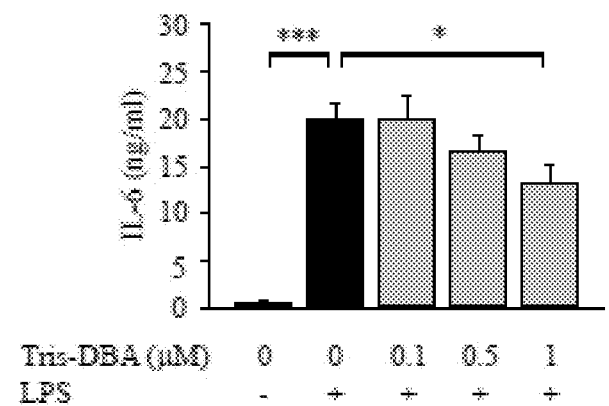
Figure 3H:
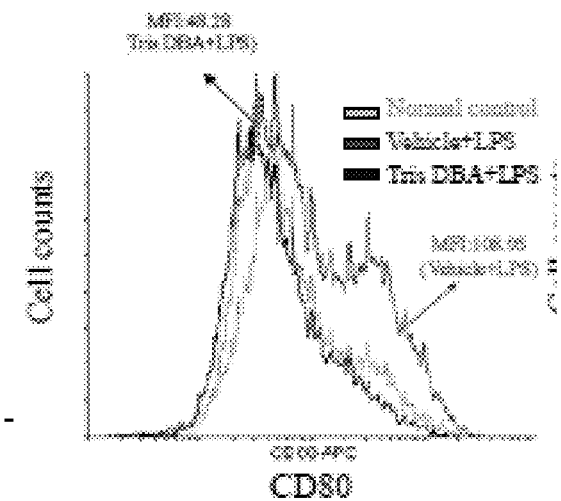
Figure 3I:
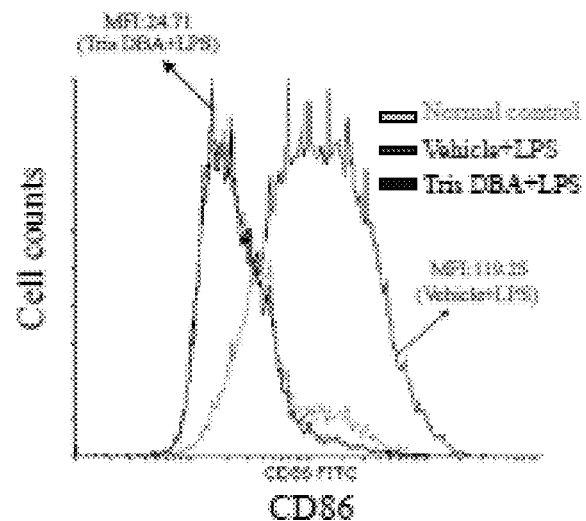
Figure 3J:
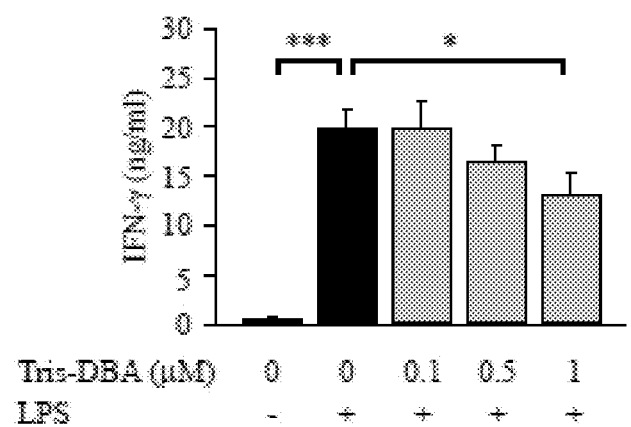
Figure 3K:
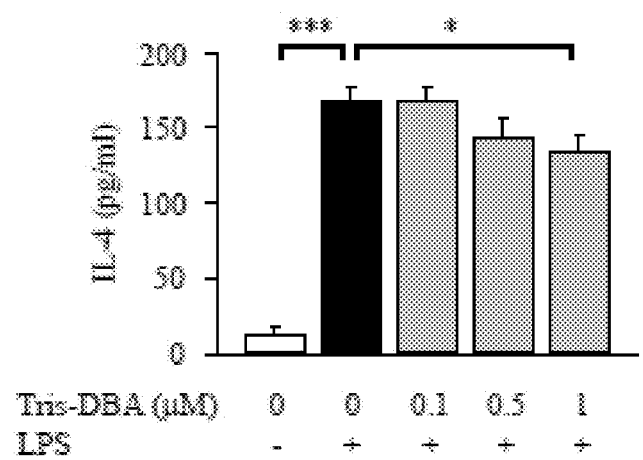
Figure 3L:
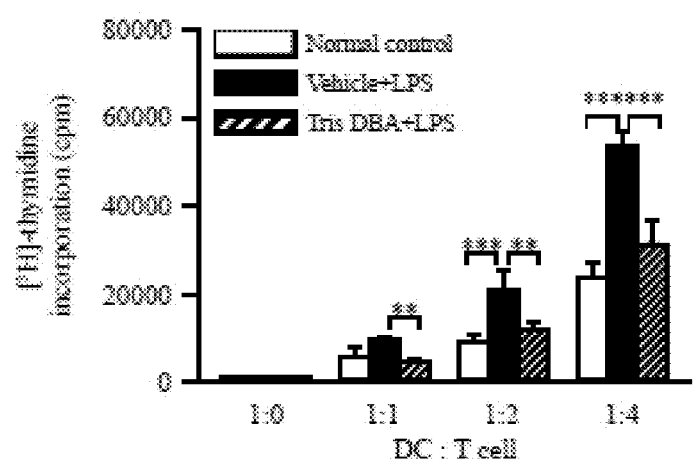

The dendritic cells are closely bound up with human immune defense mechanism. The result shows that the Tris DBA activates CD4+CD44hiCD62lo-hi and CD8+CD44hiCD62lo-hi of spleen T cells (FIGS. 3A-3B), in Week 5, Tris DBA regulated T cells FoxP3+CD25+CD4+ significantly increase (FIG. 3C), and it can inhibit T cell proliferation (FIG. 3D), Tris DBA can enhance the manifestation of IL-1β (FIG. 3E), TNF-α (FIG. 3F), IL-6 (FIG. 3G), CD80+ (FIG. 3H), CD86+ (FIG. 3I), IFN-γ (FIG. 3J) and IL-4 (FIG. 3K) in T cells, and inhibit the proliferation of T cells (FIG. 3L).

2.2 Test Urine Protein, Renal Function and Autoantibody Concentration in Serum

The mouse urine is collected weekly, and the serum is collected when the mice are sacrificed in Week 3 and Week 5, the changes in three biochemical indexes, which are creatinine (Cr), BUN and albumin/creatinine ratio (ACR) in urine, are tested according to the operational manual of commercial reagent kit, so as to analyze the changes in renal function.

When the mice are sacrificed in Week 3 and Week 5, the renal tissue is taken for analysis, the renal cortex tissue is stained by PAM to analyze the content of immunoglobulin G (IgG) and serum complement C3, and the content of F4/80+ macrophages and CD30+ T cells is analyzed by IHC, so as to detect specific antigen molecules in tissue slice and to perform positioning, qualitative and quantitative analyses.

Figure 4A:
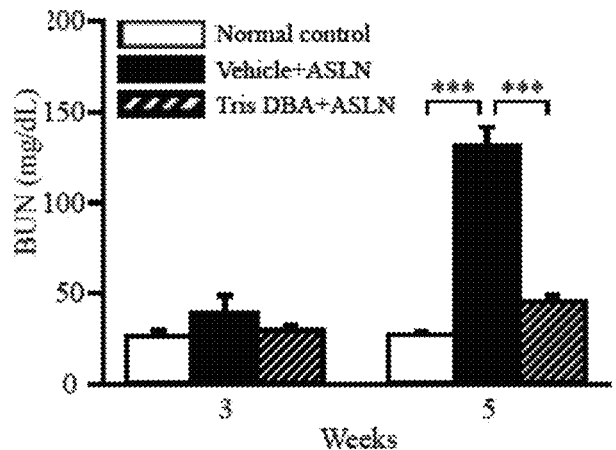
FIG. 4A shows that Tris DBA inhibits the BUN, FIG. 4B (creatinine (Cr)) and urine albumin/Cr ratio (ACR) (FIG. 4C) of ASLN mouse.
Figure 4B:
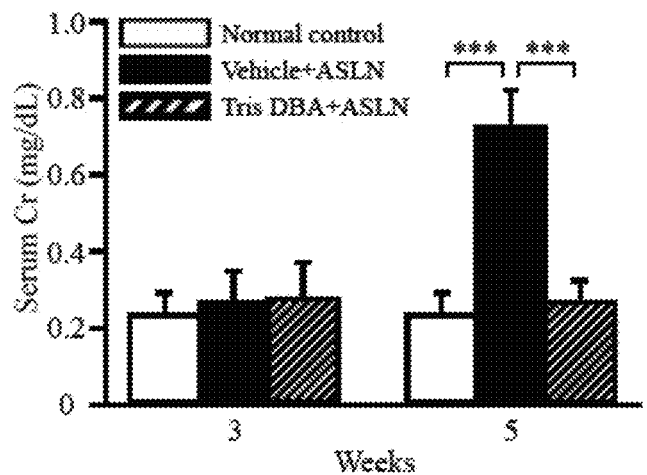
FIG. 4D shows the mouse renal tissue stained by PAM.
FIG. 4E-4J show Tris DBA inhibits ASLN mouse glomerular cell proliferation (FIG. 4E), glomerular crescent structure proliferation (FIG. 4F), neutrophilic infiltration (FIG. 4G), fibrinoid necrosis (FIG. 4H), renal interstitial inflammation (FIG. 4I) and glomerulonephritis (FIG. 4J).
FIGS. 4K and 4M shows the mouse renal tissue stained by immunohistochemistry (IHC), showing that Tris DBA inhibits the IgG (FIGS. 4K and 4L), serum complement C3 (FIG. 4N) and anti-dsDNA autoantibody (FIG. 4O) in ASLN mouse kidney.
FIGS. 4P and 4R show the renal tissue stained by IHC, it is observed that the Tris DBA obviously inhibits the quantity of F4/80+ macrophages (FIG. 4Q) and CD3+T cells (FIG. 4S) in ASLN mouse kidney.
Figure 4C:
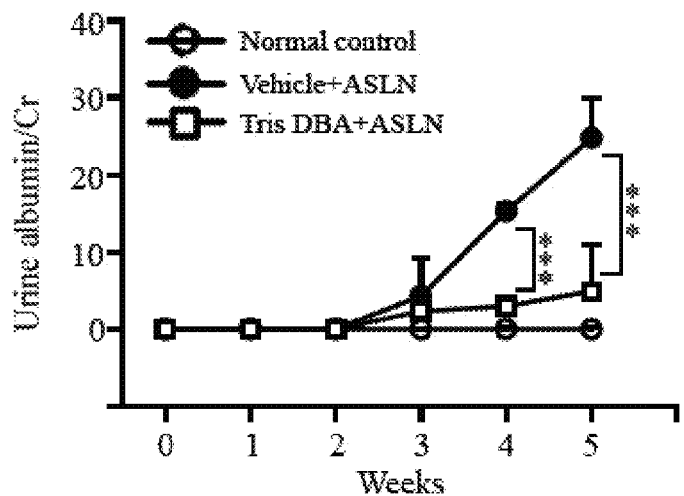

As shown in FIGS. 4A-4C, according Tris DBA to the test for the biochemical indexes related to renal function of ASLN mouse (NZB/WF1), the Tris DBA inhibits the content of BUN, urine ACR and creatinine in ASLN mouse, and there is favorable inhibitory effect in Week 3.

Figure 4D:
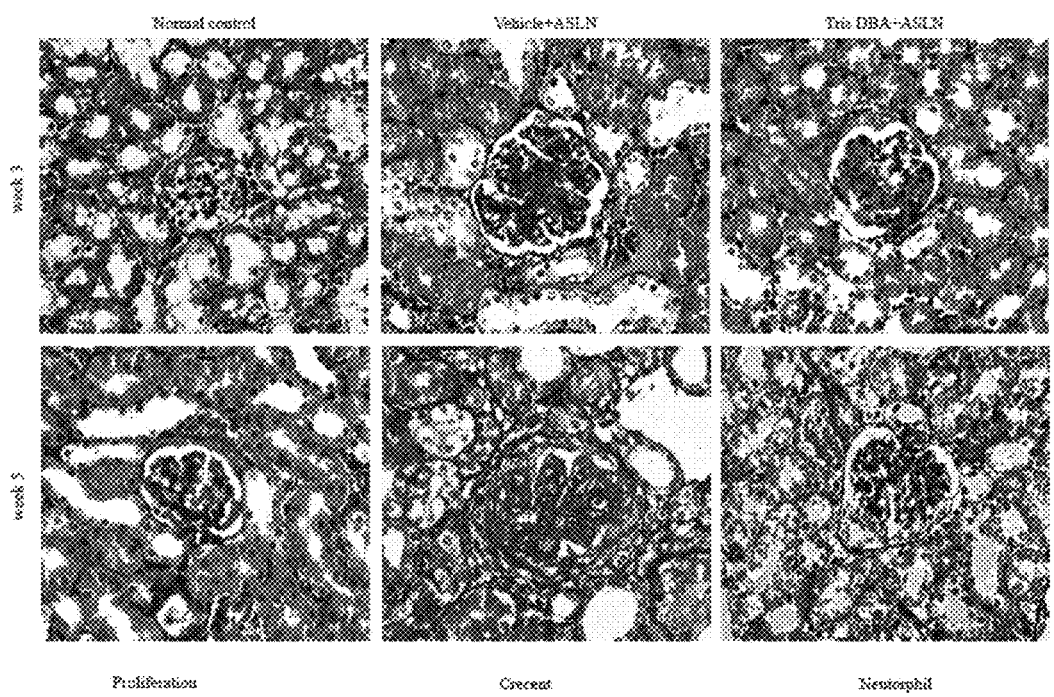
Figure 4E:
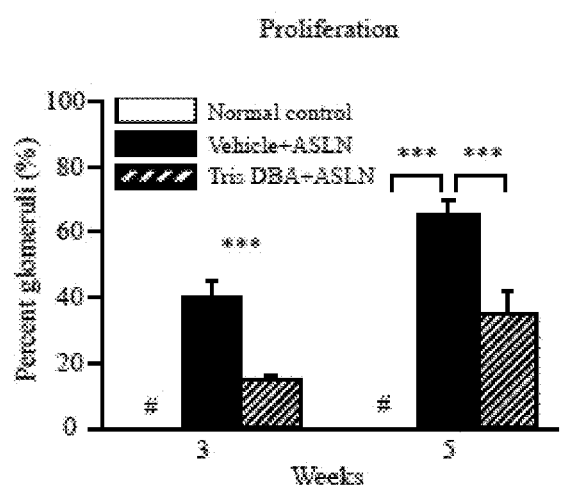
Figure 4F:
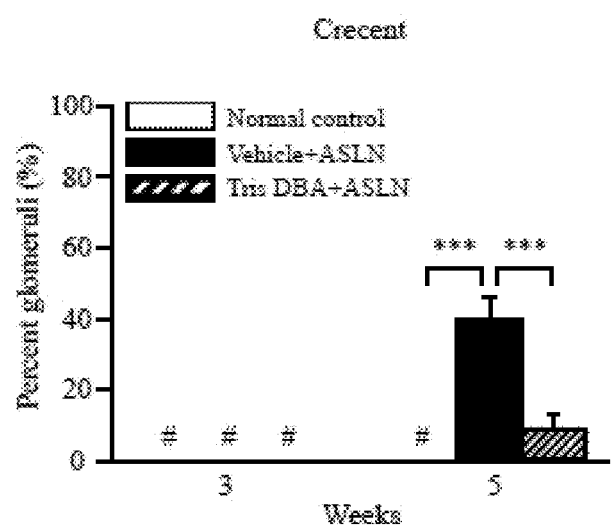
Figure 4G:
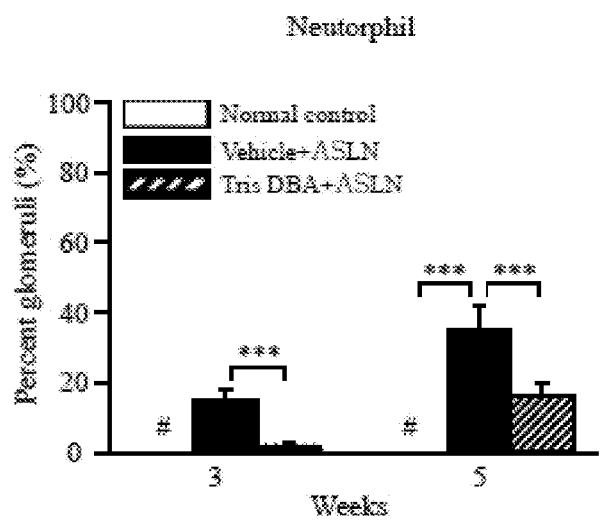
Figure 4H:
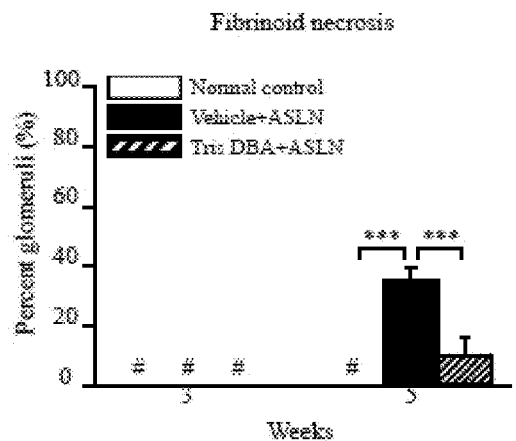
Figure 4I:
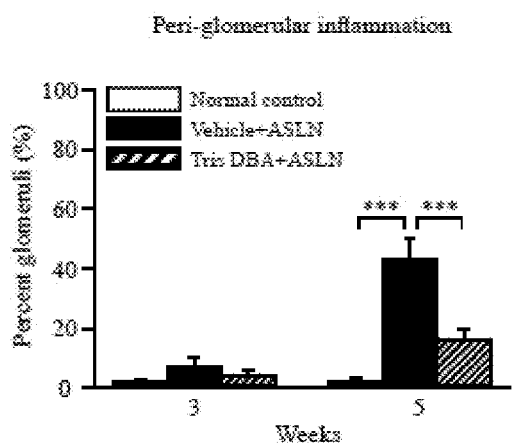
Figure 4J:
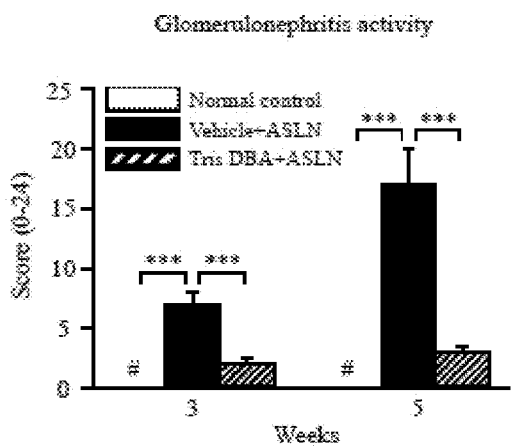

FIGS. 4D and 4I show the renal tissue stained by PAM, Tris DBA obviously inhibits the glomerular cell proliferation of ASLN mouse (FIG. 4E), glomerular crescent structure proliferation (FIG. 4F), neutrophilic infiltration (FIG. 4G), fibrinoid necrosis (FIG. 4H), renal interstitial inflammation (FIG. 4I) and glomerulonephritis (FIG. 4J).

Figure 4K:
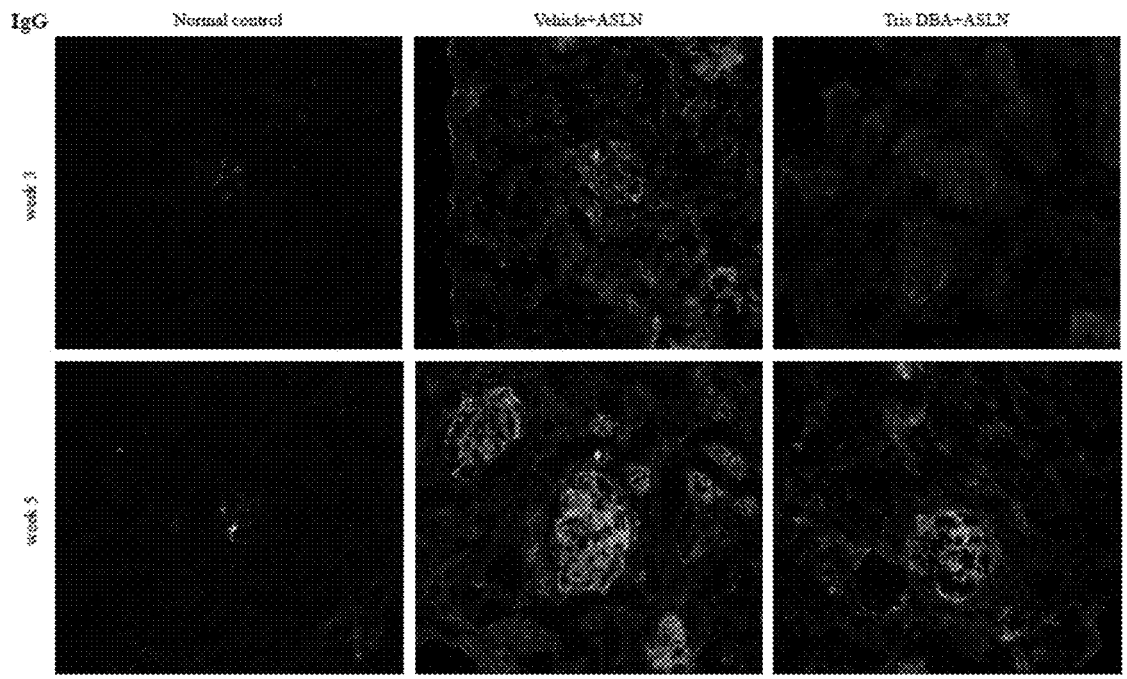
Figure 4L:
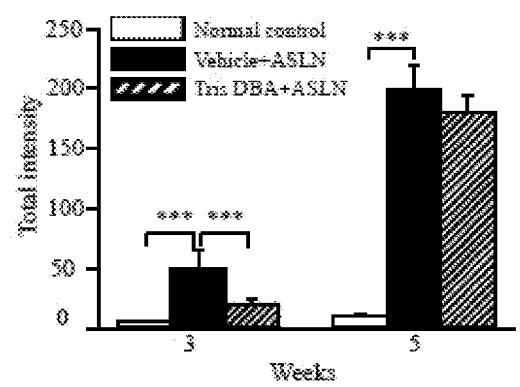
Figure 4M:
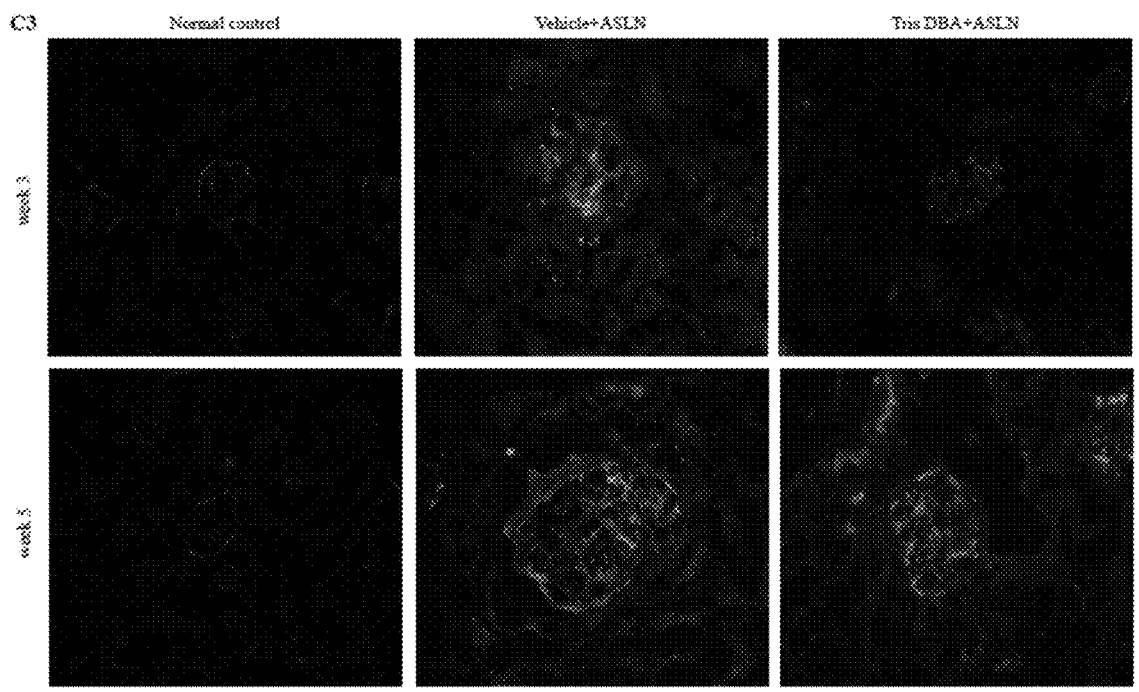
Figure 4N:
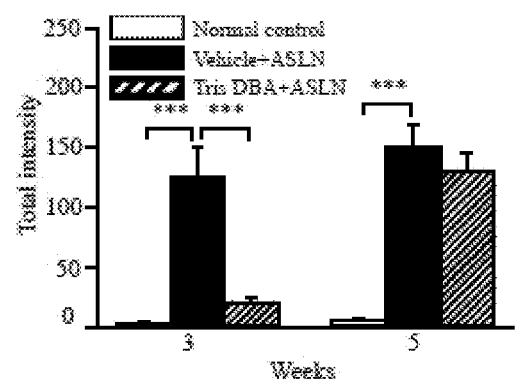
Figure 4O:
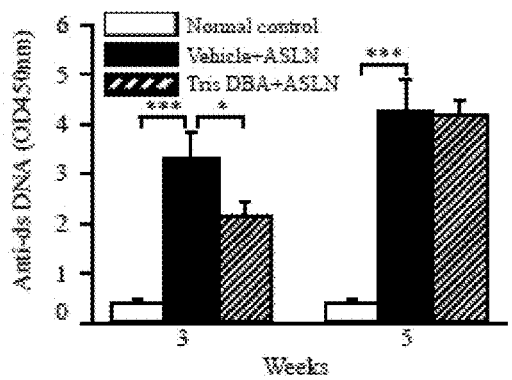
Figure 4P:
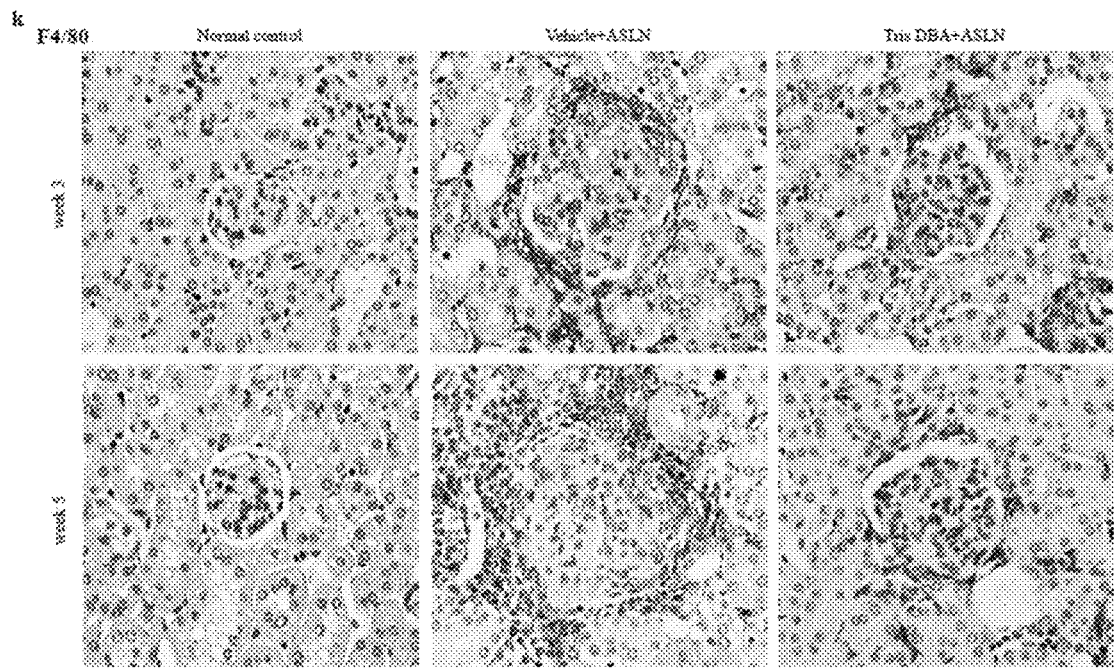
Figure 4Q:
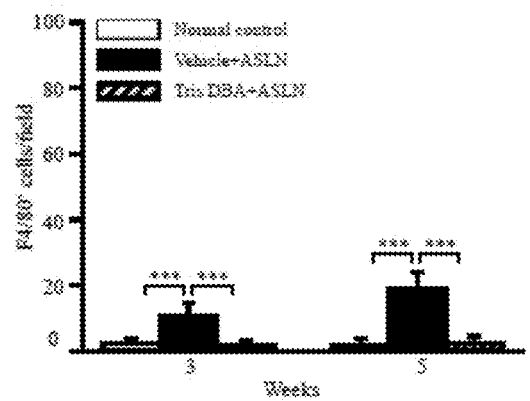
Figure 4R:
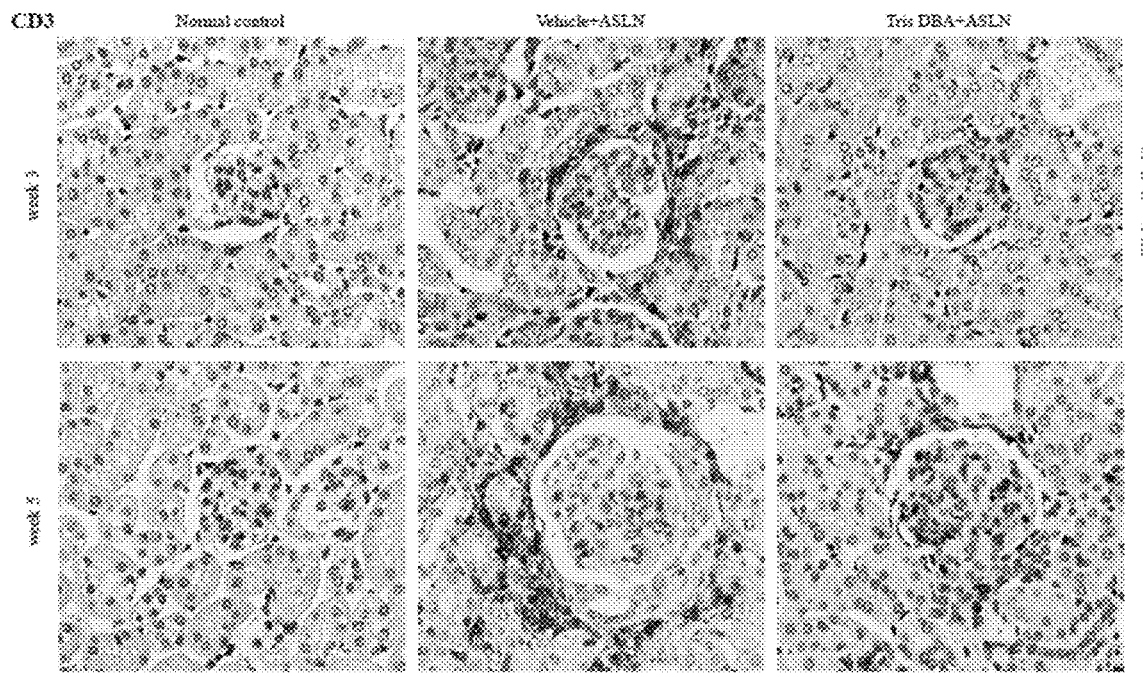
Figure 4S:
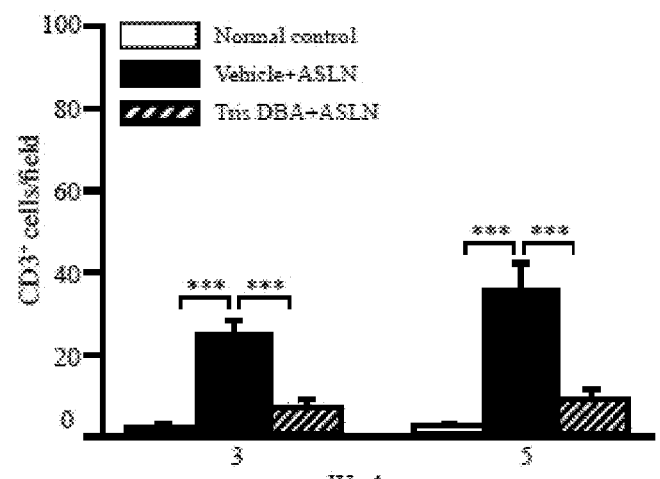

The result shows that Tris DBA can obviously inhibit the content of immunoglobulin G (IgG) (FIG. 4K-4L), serum complement C3 (FIG. 4M), F4/80+ macrophages (FIGS. 4N-4Q) and CD3+T cells (FIGS. 4R-4S) in ASLN mouse kidney.

2.3 Tris DBA Inhibits NLRP3 Inflammasome Activation

The renal tissue is thoroughly mixed with RIPA lysis, the expression levels of proteins Atg5, LC3B, p62, NLRP3, caspase-1, IL-1β, p47phox, NQO1, pERK, pJNK and pp38 are tested by gel electrophoresis (SDS-page).

The result shows that FIGS. 5A-5H show the inhibitory effect of Tris DBA on NLRP3 (FIG. 5B), IL-1β (FIG. 5C), Atg5 (FIG. 5G) and LC3B I/II (FIG. 5H) in ASLN mouse kidney.

Figure 5A:
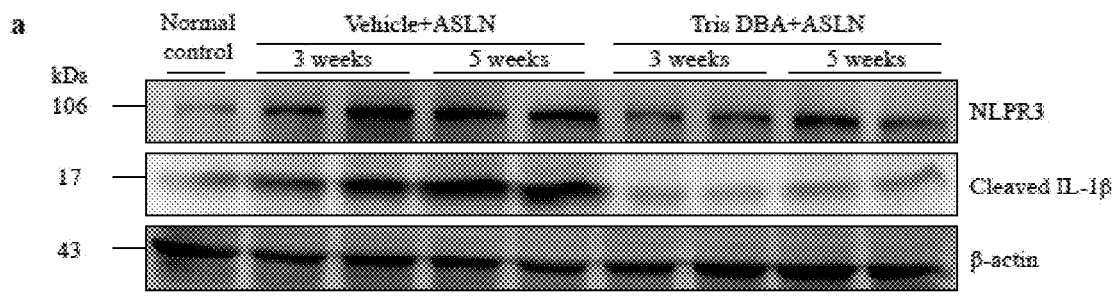
FIGS. 5A, 5D and 5F show the Western Blot resulting images, it is observed that the Tris DBA inhibits NLRP3 (FIG. 5B), IL-1β (FIG. 5C), LC3B I/II (FIGS. 5E and 5H) and Atg5 (FIG. 5G) in ASLN mouse kidney.
Figure 5B:
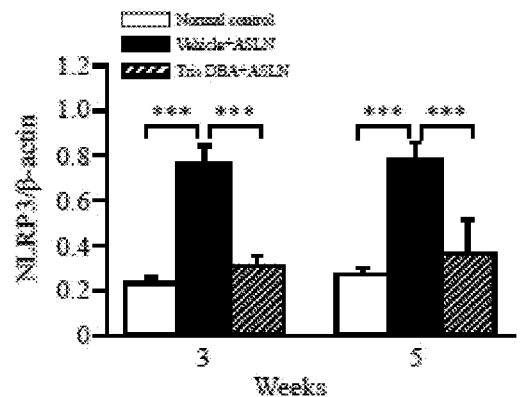
FIGS. 5I-5L show that Tris DBA can inhibit the quantity of p47NADPH in ASLN mouse kidney (FIG. 5J), Tris DBA can promote the manifestation of NQO1 (FIG. 5K), Tris DBA can enhance the activity of GPx in ASLN mouse kidney, so as to protect kidney (FIG. 5L).
Figure 5C:
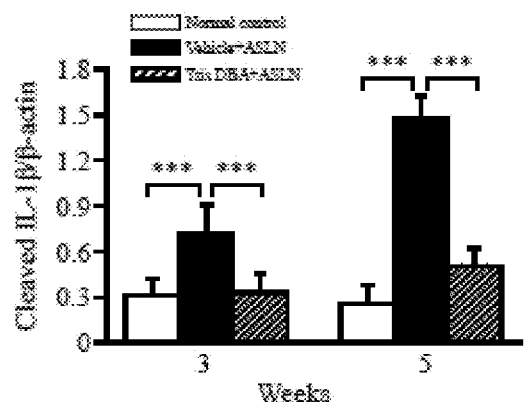
Figure 5D:
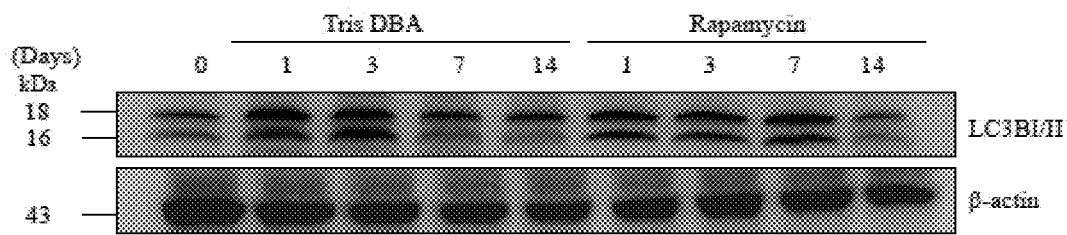
Figure 5E:
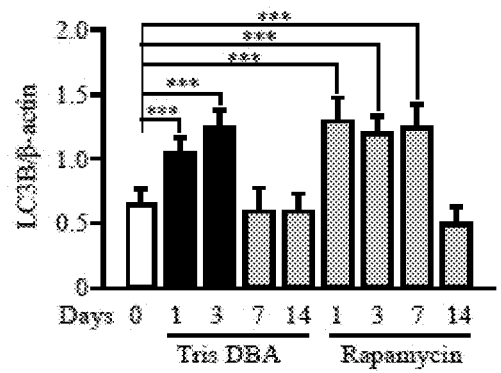
Figure 5F:
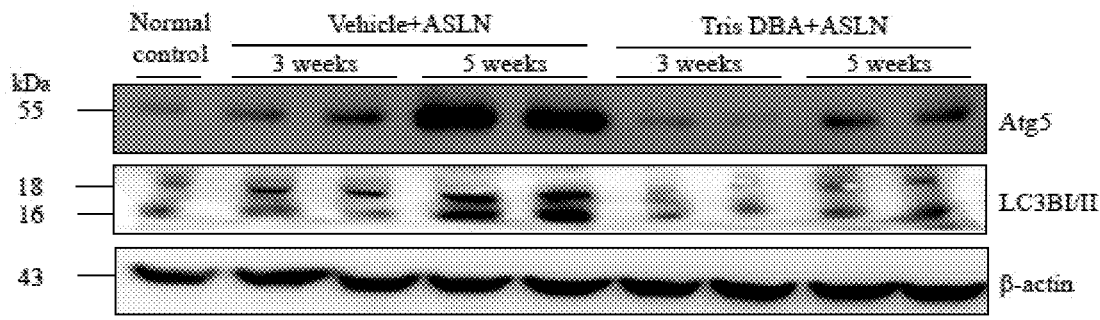
Figure 5G:
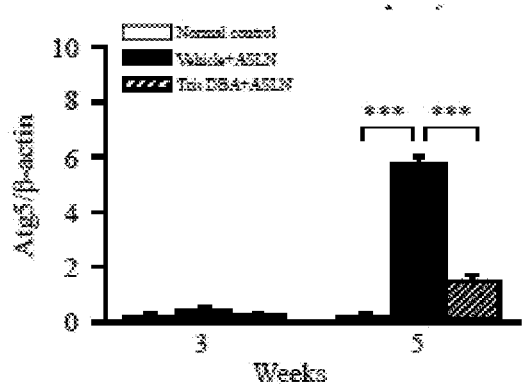
Figure 5H:
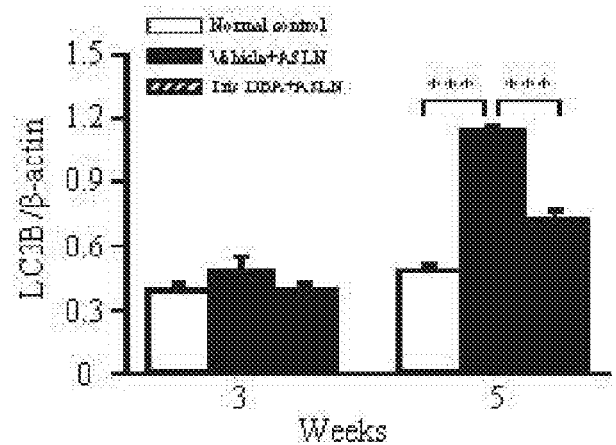
Figure 5I:
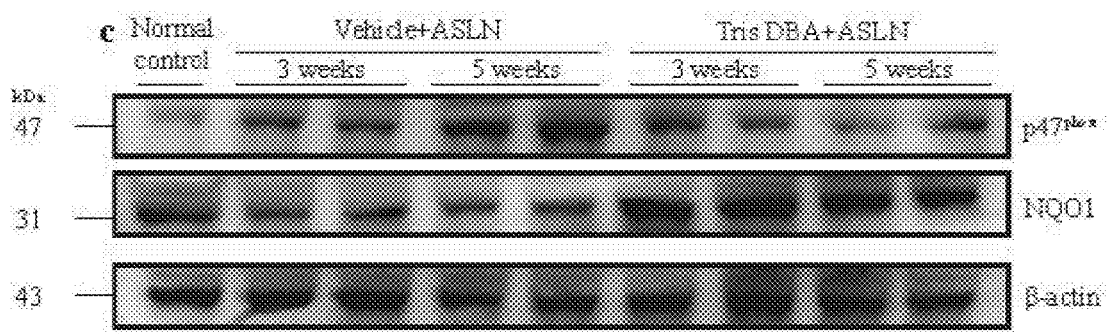
Figure 5J:
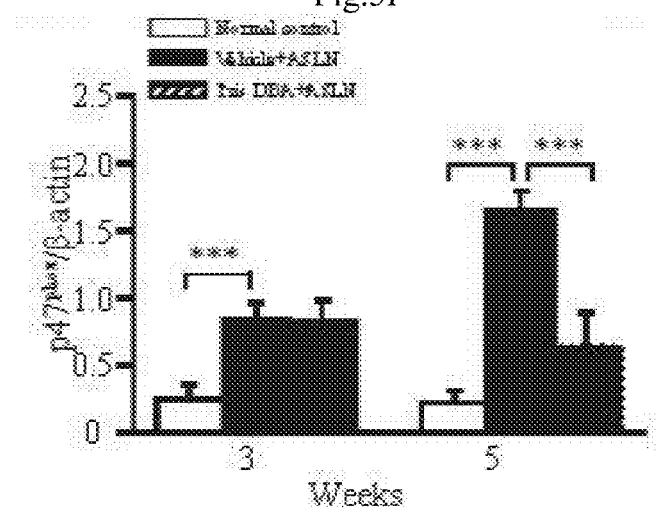
Figure 5K:
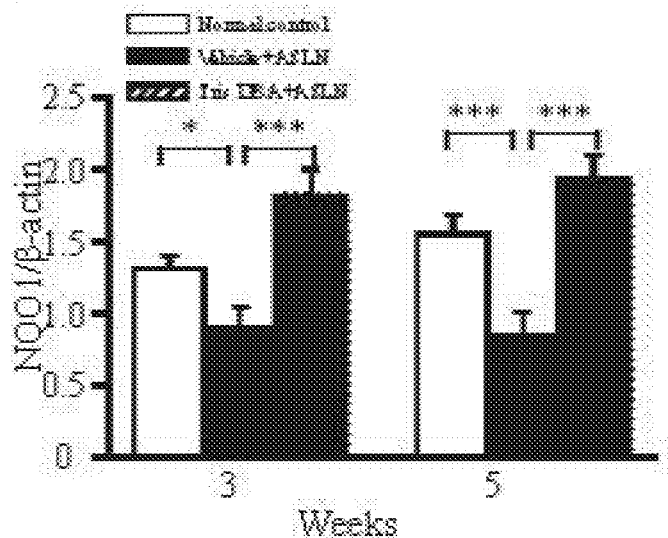
Figure 5L:
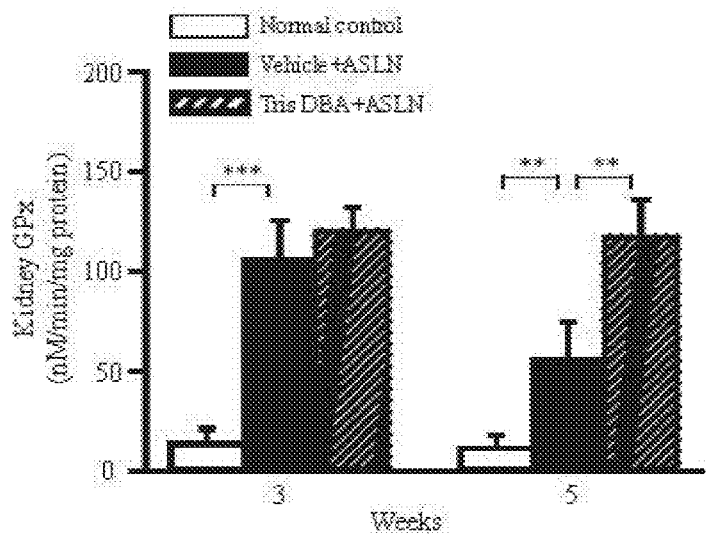

The result shows that FIGS. 5I-5L show that Tris DBA can inhibit the content of p47NADPH in ASLN mouse kidney (FIG. 5J), Tris DBA can promote the manifestation of NQO1 (FIG. 5K), Tris DBA can enhance the activity of GPx in ASLN mouse kidney, so as to protect kidney (FIG. 5L).

2.4 Test Reactive Oxygen Species (Reactive Oxygen Species; ROS) of BMDM, Serum, Urine and Tissue.

The ASLN mouse urine, serum and renal tissue obtained in Embodiment 2.4 are used to test antioxidant activity. The ROS content is tested according to operational manual of commercial reagent kit, the fluorescence probe dihydroethidium (Dihydroethidium, DHE) reacts with mouse urine and serum. The experimental results are represented as RLU/15 min/ml; the renal tissue is represented as RLU/15 min/mg dry weight.

The generation of mitochondrion ROS in the mouse BMDM is tested by using mitosox principle. There are two experimental groups (treatment group Tris DBA, negative control group NAC), reacting with 1 µg/mL LPS and cells for 5.5 hours, treated with ATP for 30 minutes, treated with commercial reagent H2DCFDA for one hour, so as to evaluate the cellular infiltration fluorescence intensity.

Figure 6A:
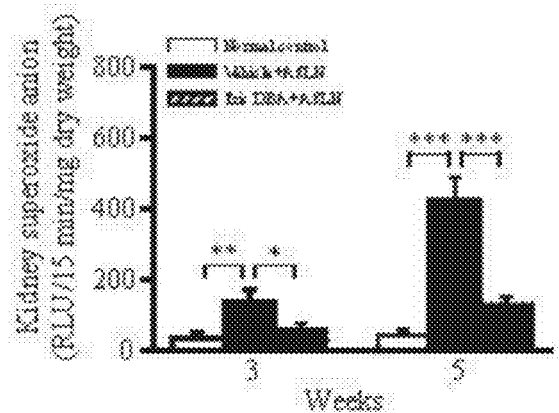
FIGS. 6A-6C show that Tris DBA can inhibit the generation of superoxide anions in ASLN mouse kidney (FIG. 6A), serum (FIG. 6B) and urine (FIG. 6C).
Figure 6B:
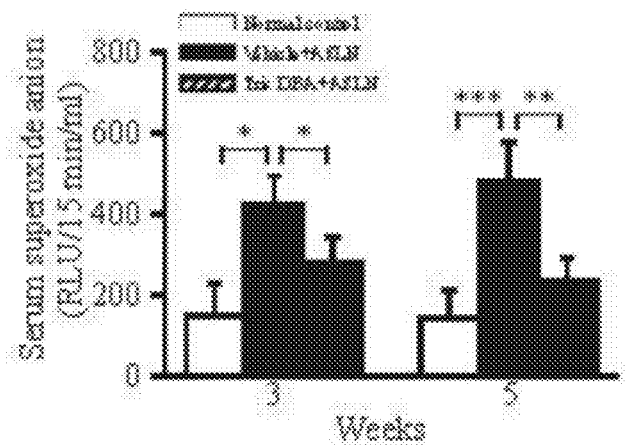
Figure 6C:
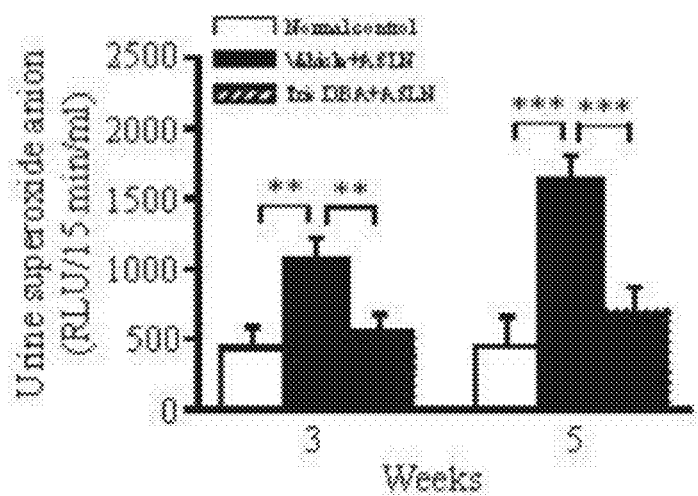

As shown in FIGS. 6A-6C, the results show that in Week 3 and Week 5, the Tris DBA group has lower expression level of superoxide anion than Katimin-1® group, and the mouse given Tris DBA is obviously close to control group.

Figure 6D:
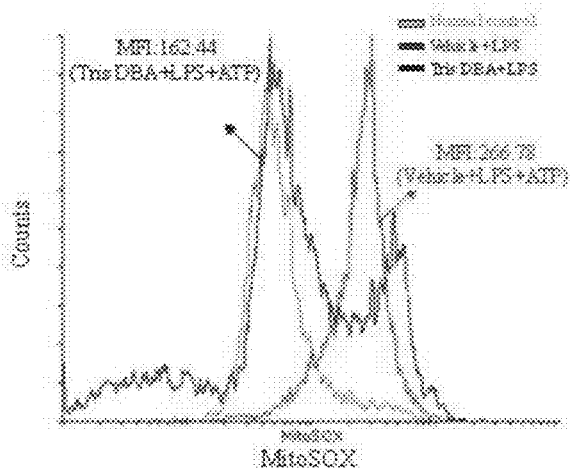
FIGS. 6D-6E show that Tris DBA can inhibit the generation of mitochondria ROS in BMDM cells.
Figure 6E:
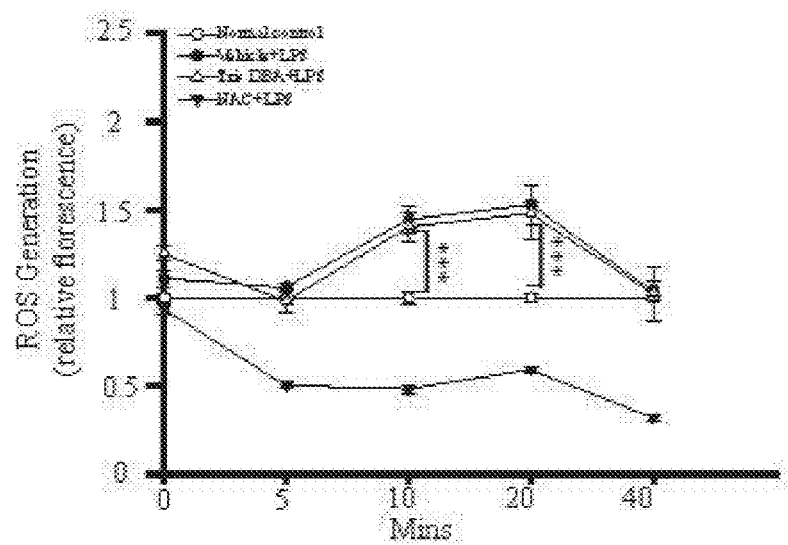

As shown in FIGS. 6D-6E, the results show that Tris DBA can inhibit the generation of mitochondria ROS in BMDM cells.

To sum up, the function of Tris DBA to inhibit T cells is induced by bone marrow differentiated dendritic cells and it can inhibit the generation of anti-dsDNA autoantibody in aggravated lupus nephritis mouse model, and promote autophagy to inhibit the activation of NLRP3 inflammasome, and to inhibit the phosphorylation of JNK, ERK and p38MAPK information paths. In terms of effective mechanism of Tris DBA, the phosphorylation of MAPK (JNK, ERK) is inhibited to regulate the first information transfer path of NLRP3 inflammation path and autophagy and to inhibit the activation of NLRP3 inflammasome. The results show that Tris DBA can be a preventive and candidate drug for treating lupus nephritis, especially for disease deterioration.

All the features disclosed in the invention shall be implemented in any combinational forms. Each feature disclosed in the present invention shall be replaced by substitutes for the same, equal or similar purposes. Therefore, unless otherwise specified, each feature is merely an embodiment of a category of equipollent or similar features.

The invention claimed is:

1. A method for treating an active lupus nephritis with higher NLRP3 inflammasome via mediated priming signal of the NLRP3 inflammasome and regulating the autophagy/NLRP3 inflammasome axis, comprising administering an effective dose of a pharmaceutical composition comprising Tris DBA, wherein the Tris DBA inhibits glomerular cell proliferation, inhibits glomerular crescent structure proliferation, inhibits neutrophilic infiltration, inhibits fibrinoid necrosis, inhibits renal interstitial inflammation and glomerulonephritis, wherein the Tris DBA inhibits NLRP3 inflammasome activation, wherein the Tris DBA inhibits the proliferation of CD4+ memory T cells and CD8+ memory T cells in a subject of active lupus nephritis with higher NLRP3 inflammasome, wherein the effective dose of the Tris DBA administered to the subject being a mouse is 10-20 mg/kg, wherein the effective dose of the Tris DBA administered to the subject being a human is 600-1200 mg/kg.

2. The method of claim 1, wherein the Tris DBA promotes antioxidation of cells in the subject of active lupus nephritis with higher NLRP3 inflammasome.

3. The method of claim 1, wherein the pharmaceutical composition of the form comprising granule, capsule, pastille, powder, solution and/or suspension.

4. The method of claim 1, wherein the pharmaceutical composition is orally administered.

\* \* \* \* \*